United States Patent
Larsen et al.

(10) Patent No.: US 6,225,108 B1
(45) Date of Patent: *May 1, 2001

(54) MICROSENSOR FOR MEASURING THE CONCENTRATION OF A MEDIUM IN AN ENVIRONMENT

(76) Inventors: Lars Hauer Larsen, Overdrevet 25, DK-8382 Hinnerup; Niels Peter Revsbech, Thorshavnsgade 3, DK-8200 Århus N; Thomas Kjær, Lollandsgade 63, DK-8000 Århus C, all of (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/297,951
(22) PCT Filed: Nov. 10, 1997
(86) PCT No.: PCT/DK97/00512
§ 371 Date: May 7, 1999
§ 102(e) Date: May 7, 1999
(87) PCT Pub. No.: WO98/21309
PCT Pub. Date: May 22, 1998

(30) Foreign Application Priority Data

Nov. 12, 1996 (DK) .................................................. 1265/96

(51) Int. Cl.$^7$ ....................................................... C12M 3/00
(52) U.S. Cl. ..................................... 435/287.1; 435/287.5; 435/288.7; 435/808; 435/817; 204/403; 204/415
(58) Field of Search ..................................... 435/4, 29, 30, 435/37, 287.1, 287.5, 287.7, 288.8, 817, 808; 204/403, 415; 422/68.1, 82.01, 82.05, 82.06, 82.07

(56) References Cited

U.S. PATENT DOCUMENTS 5,104,804 * 4/1992 Humphries et al. .
5,776,715 * 7/1998 Garnham ................................. 435/8
6,030,828 * 2/2000 Damgaard et al. ............... 435/287.1

FOREIGN PATENT DOCUMENTS

95/33068 * 12/1995 (WO) .
97/19345 * 5/1997 (WO) .

OTHER PUBLICATIONS

Kobos Et Al. 'Bacterial Membrane Electrode for the Determination of Nitrate.' Anal. Chem. vol. 51, No. 8 (Jul. 1979), pp. 1122–1125.*

Larsen Et Al. 'A Microsensor for Nitrate Based on Immobilized Denitrifying Bacteria.' Appl. Environ. Microbio. vol. 62, No. 4 (Apr. 1996), pp. 1248–1251.*

Larsen Et Al. 'A Microscale NO3–Biosensor for Environmental Applications.' Anal. Chem. vol. 69, No. 17 (Sep. 1, 1997), pp. 3527–3531.*

* cited by examiner

Primary Examiner—William H. Beisner
(74) Attorney, Agent, or Firm—Lee, Mann, Smith, McWilliams, Sweeney & Ohlson (57) ABSTRACT

The invention relates to a microsensor for the measurement of the presence and the concentration of a primary medium, for example nitrate, in an environment where the microsensor is placed. The microsensor has a casing which surrounds a transducer and a reservoir containing nutrients. The transducer has a tip placed at a distance from the opening of the casing. Between the transducer tip and the opening is a reaction chamber with bacteria. The bacteria metabolises the primary medium (nitrate) into a secondary medium (nitrous oxide) which is detected by the transducer. The casing has a passage that stretches to the reservoir behind the transducer tip. Through the passage nutrients are fed to the bacteria whereby their activity can be maintained.

19 Claims, 5 Drawing Sheets

MICROSENSOR FOR MEASURING THE CONCENTRATION OF A MEDIUM IN AN ENVIRONMENT

The present invention relates to a microsensor for measuring the concentration of a primary medium in an environment, e.g. a liquid, gas or matrix, which microsensor has a transducer and a reaction chamber with an opening. This microsensor is of a type, which has a a casing or container around the transducer. The microsensor is provided with an opening, and the tip of the transducer is placed at a certain distance from this opening. Between the opening and the tip, a reaction chamber is formed. Furthermore, the invention relates to the application of such microsensor.

According to the invention, the microsensor is primarily intended to measure the presence and concentration of nitrate, $NO_3^-$. In the following, nitrate is also called the primary medium, the presence and concentration of which is to be determined. This determination is of interest in connection with the analysis of the conversion of nitrate in agricultural cultivation. Also, the nitrate concentration is of interest when determining the degree of pollution of surface water, groundwater and waste water. However, the inventive microsensor can also be used to measure the presence and concentration of other substances, like sulphate, $SO_4^{2-}$.

"Applied and Environmental Microbiology", Apr. 1996, page 1248–1251, describes a microsensor which can measure the presence and concentration of nitrate. Here, the primary medium is nitrate, and measurement of its concentration is done indirectly through measurement of a concentration of a secondary medium which is nitrous oxide, $N_2O$. Nitrous oxide develops as the secondary medium after reduction of the primary medium nitrate, $NO_3^-$ and the reduction is carried out due to denitrifying bacteria.

The known microsensor has a transducer with a tip. A housing or casing surrounds the transducer, and has an opening. Between the opening of the container and the tip of the transducer a reaction chamber whith bacteria is located. The bacteria are immobilized in the reaction chamber by means of an alginate matrix. The casing is fixed to the transducer by means of wax that is placed between the transducer and the container.

This known microsensor suffers from some disadvantages. Measurements with the known microsensor can only be performed in environments having nutrients for the bacteria, or their activity will cease. Nutrition of the bacteria in environments devoid of dissolved nutrients in this prior art reference is based on granules of glycogen or polyhydroxybutyrate contained within the bacteria used. However, these granules are exhausted after about 1–2 hours without an added electron donor.

The range of measurement and the response time for the known sensor are linearly proportional. Hence this sensor cannot be used for measurements in environments with $NO_3^-$ concentration exceeding 500 $\mu M$. Furthermore, it is not at all possible to increase the relation between the $NO_3^-$ concentration in the measuring environment and the $N_2O$ concentration at the transducer, and, consequently, it is not possible to have the measuring range of the microsensor exceed 5–500 $\mu M$ $NO_3^-$. Therefore, the known microsensor is unfit for measuring the presence and the concentration of e.g. nitrate in natural environments.

Other known sensors are the ion-exchanger based sensors which are intended for measuring nitrate in a liquid. However, this type of sensor suffers from one essential disadvantage. Its sensitivity to interference from other ions like cloride, $Cl^-$ and hydrogen carbonate, $HCO_3^-$, contributes to errors in measurements performed with this type of sensor. This known sensor is, therefore, unfit for measurements in e.g. sea water and alcaline water like groundwater or surface water. Furthermore, the sensitivity towards $HCO_3^-$ interference means, that the ion-exchanger based sensors suffers from pronounced interference in biological very active environments with extensive production of $HCO_3^-$ such as waste water treatment plants.

From the Japanese patent application JP 60117143 a design of a sensor is known, in which enzymes are fed from a separate, external reservoir through a tube down to an immobilized enzyme membrane. In this way, the enzymes are kept active hence prolonging the period of activity of the sensor. However, the external reservoir and the projecting tube makes this sensor larger and more vulnerable to mechanical influences compared to the inventive design with only one single, outer casing. Further, this sensor is not a self contained unit; supply of enzymes comes from a external source with the function of replenishing.

The aim of the present invention is to provide a sensor, which does not suffer from the known disadvantages, and by means of which the measurement of the concentration of a primary medium, i.e. nitrate $NO_3^-$, will become more precise and results in less sensitivity against interference from other substances.

Another aim of the invention is to provide a sensor using the principle of metabolism through bacteria, which sensor has an extended life span, is handy and robust and does not need manual replenishment of the bacteria or their nutrients.

As described in claim 1, these aims are reached by using af microsensor of the type using bacteria for transforming a primary medium into a secondary medium and detecting the secondary medium as an indirect measure of the primary medium, whereby the bacteria are confined in a reaction chamber which is surrounded by an outer casing. The microsensor is characterised in that the casing delimits a chamber or reservoir containing nutrients, and thus confines the nutrients which rests against the casing, preferably directly, and that a passage is located between reaction chamber and reservoir. Through this passage nutrients diffuse from the reservoir to the reaction chamber, to be consumed by the bacteria, and through which passage also secondary medium diffuses away, i.e. in a direction opposite to the direction of the nutrient.

The invention thus solves the problem of nutrition of the denitrifying bacteria placed in the reaction chamber. By providing a reservoir with nutrients confined by the casing and a passage leading from the reservoir to the reaction chamber, a self contained regenerative sensor is achieved. The reservoir functions as an internal constant diffusive source of nutrients which regenerates the bacteria by allowing continous growth in the tip of the sensor. The reaction chamber thus functions as a true micro chemostat. Preferably, according to claim 2, the casing surrounds both reservoir and reaction chamber whereby a practical, self cointained entity can be manufactured. As described in claim 3, the passage is preferably located between the transducer and the casing, which results in a narrow channel through which nutrients are fed. As mentionend in claim 4, the nutrient placed in the reservoir should contain either an electron acceptor or donor dependent upon whether the primary medium is oxidized or reduced by the the biologically active substance in the reaction chamber.

As further stated in claim 5, the passage can contain means for influencing the net flux of molecules. In a situation with varying concentration of the primary medium, it is important to guide or influence the diffusion. A sudden decrease in the concentration of the primary medium in e.g. the sea water would cause a reversal in the direction of natural diffusion of secondary medium. Instead, accumulated secondary medium would now diffuse from the reservoir to reaction chamber, resulting in incorrcet measuring. By adding certain means to the passage, this situation can be avoided.

By letting the passage end up in a reservoir in the casing behind the transducer tip, an advantage is achieved in that the passage can be used for adding nutrients to the bacteria in order to maintain the bacterial activity. In establishing a passage which stretches behind the transducer tip, essential improvements are achieved when measuring the presence and the concentration of e.g. nitrate in the environment.

The transducer is of a known type, a so-called Clark type which is electro-chemical and consists of a glass capillary with a tip, but quite different transducer types, like a fibre optic transducer known from the art, can also be used with the invention. At the tip of the Clark type sensor is an opening, where a gas permeable silicone plug or membrane is inserted. In the glass capillary right behind the plug is a silver cathode, but other kinds of cathodes can be used too. The ion-permeable membrane is preferably made of an non degradeable polymer. However, other kinds of ion-permeable material can also be used.

A nutrient medium has been added to the inventive microsensor. If the primary medium is a negatively loaded ion, it may be advantagous to add to the nutrient placed in the reservoir a salt with a low migration speed of positive ions, like LiCl. If the primary medium is a positively loaded ion, the salt added to the nutrient should contain negative ions with low migration speed, e.g. $KH_2PO_4$.

The microsensor is based on bacterial activity resulting in production of the secondary medium by transformation of the primary medium. According to the invention the microsensor is primarily intended for detecting the presence of nitrate, and also measuring the concentration of nitrate as the primary medium, by using the activity of denitrifying bacteria. These bacteria lacks the $N_2O$ reductase enzyme, and can be bacteria from the genus Agrobacterium Radiobacter. Through the bacterial activity nitrate, $NO_3^-$, is metabolised by reduction to nitrous oxide, $N_2O$. A certain quantity of nitrous oxide diffuses into the transducer and is reduced at the transducer cathode. The quantity of nitrous oxide that is reduced at the transducer cathode is directly proportional to the $NO_3^-$ concentration in the environment where measurement takes place.

In another preferred embodiment as stated in claim 6, the microsensor is characterized in that the conicity in a reservoir behind the transducer tip exceeds that of the reaction chamber. The passage ends up in a volumen in the casing, where this volumen stretches behind the transducer tip and where the upper part of the casing has a conicity exceeding that of the reaction chamber part. This is advantageous because of the relatively greater increase in volumen in the upper part compared to the increase in volumen of the reaction chamber part. This measure results in a dilution of the small fraction of the nitrous oxide which diffusies to the reservoir through the passage. This diffusion of surplus nitrous oxide through the passage into the volumen stretching behind the transducer tip will, therefore, not result in a significant accumulation of $N_2O$ behind the transducer tip. Such an accumulation would otherwise contribute with an erroneous bagground signal. Preferably, as mentioned in claim 7, only the upper part of the casing is conical, whereas the lower part enclosing the reaction chamber has parallel or almost parallel sides.

When using a microsensor according to the invention, other substances in the environment than nitrate, $NO_3^-$, will not influence the measurements particularly. In addition to nitrate, nitrite $NO_2^-$, and nitrous oxide $N_2O$ from the outer environment will contribute with an error to the measuring results if the sensor is subject to change in the consentration in the interfering agent. They will contribute to a signal from the transducer with a factor 1 and a factor 2, respectively, compared to the signal for a corresponding concentration of nitrate. However, the nitrite and nitrous oxide contents are very small in the most environments where the inventive microsensor is to be used. Often (e.g., in waste water treatment systems)it is an advantage to integrate nitrite and nitrate in one signal. The low sensitivity to interference from other substances means that the microsensor can be used for measurements in sea water in spite of the presence of other ions, as for example chloride $Cl^-$ in sea water.

The microsensor is only to a small degree sensitive to stirring in the environment where measurements are performed. Furthermore, the microsensor has low sensitivity to the temperature in the environment where measurements take place. A fall in temperature in the environment will cause a reduction of the bacterial activity. However, measurements are ensured as long as the bacterial activity is able to metabolise the primary medium into a secondary medium, as for example transformation of nitrate into nitrous oxide. At a temperature of 5° C. or below the bacterial activity will be close to zero and the microsensor will therefore not be able to measure at temperatures below 3° C. However, bacteria can be isolated that are less sensitive to cold so that the microsensor will be able to measure at temperatures considerably below 3° C. The temperature of the environment is only of importance in relation to the temperature for which the transducer is calibrated, but calibration for different temperatures can be performed. In one embodiment of the microsensor this calibration may be provided with a temperature sensor for measuring the temperature at the same time as the concentration of the primary medium, for example nitrate, is being measured.

The microsensor according to the invention can measure the presence and the concentration of nitrate from 1 $\mu$M and upwards. The measuring range of concentrations of nitrate depends on the design of the microsensor.

The reaction chamber between the opening of the casing and the transducer tip can have different sizes. In order to keep the response time for the microsensor within acceptable and practical limits, a length of about 400 $\mu$M for the distance between the opening of the casing and the transducer tip will in practice be a preferable maximum size for the reaction chamber. For reaction chambers having a larger distance between the opening of the casing and the transducer tip the response time will increase considerably. If the reaction chamber has a larger distance between the transducer tip and the opening the sensitivity is reduced, but the measuring range where the sensor can be used, will be extended. Furthermore, an increase in conicity of the reaction chamber means an increased response time, an extended measuring range and a reduced sensitivity. It is, therefore, possible to achieve an optimum response time of the sensor, the sensitivity, the diameter and measuring range, dependent on a specific task of measurement.

In an embodiment of the microsensor described in claim 8, the microsensor has a "window" which stretches around the transducer. The window is inserted in the passage and facilitates the diffusion of the secondary medium. The window is made through the use of an additional casing, which surrounds the transducer and is placed between the outer casing and the transducer. The additional casing is located in a position behind the transducer tip and contains a gas, which is mainly oxygen-free and is intended for carrying away the secondary medium quicker than would be the case in the outer casing or reservoir alone. This is mentioned in claim 9. Due to the higher diffusion rate in gasses compared to liquids, carrying away the secondary medium will be quicker in gasses than in liquids. This window-design can be used together with the conicity of the outer casing or, if a space saving slim line design is wanted, without the outer case having any conicity at all, as stated in claim 10. Hence the passage would be a long channel, the walls being defined by the window on one side and the outer casing on the other. With such a design, only a small part of the secondary medium would diffuse into the reservoir.

In a preferred embodiment described in claim 11, the microsensor is characterized in that the reaction chamber contains nitrate reducing bacteria, that the primary medium is nitrate, that the secondary medium is nitrous oxide, that the bacteria reduces nitrate through production of nitrous oxide and that the transducer is a $N_2O$ transducer.

Claim 12 and 13 describes two possible types of sensors or detectors.

In another preferred embodiment described in claim 14, a microsensor according to the invention the opening of the casing has a membrane. The membrane in the opening of the casing confines the bacteria inside the reaction chamber and prevents undesired microorganisms to invade the reaction chamber.

Claim 15 describes the application of the inventive microsensor for the measurement of nitrate.

Claim 16 describes a microsensor, which is characterized by having a passage and a reservoir, whereby the reservoir is essentially free of secondary medium. Claims 17–21 describes practical designs of the microsensor according to claim 16.

A preferred method for measuring the concentration of a medium in an evironment, especially measurement of nitrate, is also described. By using Ficks Law on diffusion, a model of the diffusion processes in the reaction chamber can be made.

The invention will hereafter be described more detailed referring to the enclosed drawings.

Figure 1:
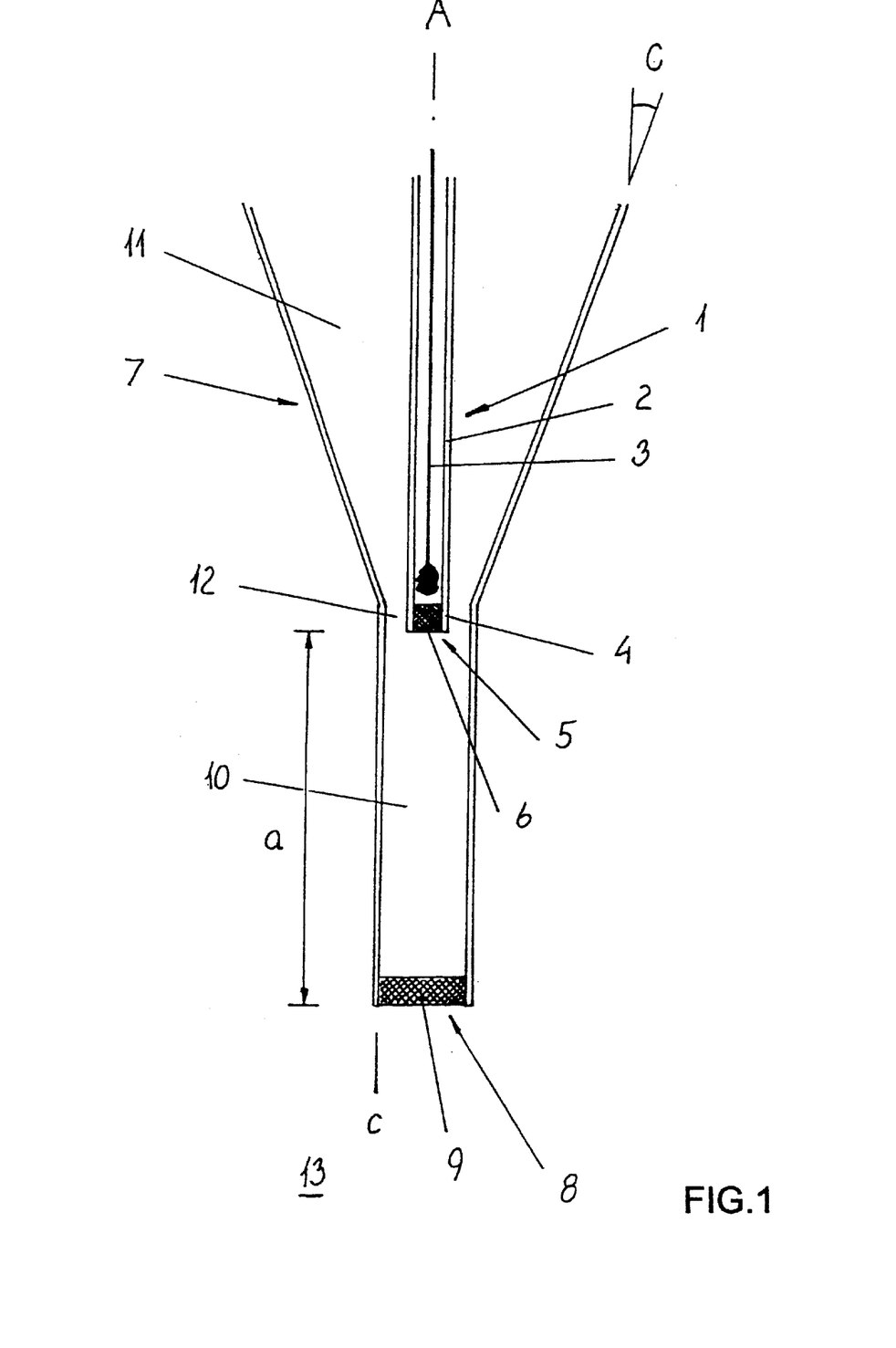
FIG. 1 A drawing showing a first embodiment of the microsensor according to the invention.

FIG. 1 shows a first embodiment for a microsensor according to the invention. The microsensor has a transducer 1. The transducer 1 has a glas capillary 2, having a cathode 3 which in the shown embodiment is a silver cathode. The glas capillary 2 has a tip 4 with an opening 5. In the opening 5 is a plug made of silicone. A casing 7—in the shown embodiment made of glas or plast—surrounds the transducer 1. The casing 7 has an opening 8 with a membrane 9 placed in the opening. This membrane 9 is made of titanium oxide, $TiO_2$. The opening 8 is placed at a distance a from tip 4 of the transducer 1. In the casing 7 between the tip 4 of the transducer I and the opening 8 of casing 7 is a reaction chamber 10. In the casing 7 behind the tip 4 of the transducer 1 is a chamber or reservoir 11 which through a passage 12 has connection to the reaction chamber 10.

The reaction chamber 10 contains active bacteria, which are supplied with nutrients through the passage 12 from the reservoir 11. In this way, sufficient bacterial activity can be maintained in the microsensor without the need of adding nutrients from outside. The microsensor is a self contained entity with its own storage of food for the bacteria. The nutrients are fed to the reaction chamber through the passage 12 by way of diffusion. The active bacteria transforms or metabolises a primary medium from an environment 13 outside the membrane 9 which has diffused into the reaction chamber 10. The metabolism results in the production of a secondary medium which is detected by the transducer 1.

Besides the traffic of nutrients and small amounts of surplus secondary medium in the passage 12, also inactive, dying or surplus bacteria from the reaction chamber 10 moves through the passage into the reservoir 11. This is due to the continous growth of the bacteria which, had it not been for the passage 12, would result in a deflection of the membrane 9 until it would burst, hereby destroying the microsensor. In this way, the passage also functions as a pressure relief.

Between the transducer 1 and the casing 7 the passage 12, is leading from the reaction chamber 10 to the reservoir 11, which is placed behind the tip 4 of the transducer 1. By means of the passage 12 any surplus of the secondary medium produced during the bacterial activity and which is not consumed by the transducer 1, can diffuse through the passage 12 to the reservoir 11. The passage 12 does not incorporate any barrier, and movement through the passage happens by way of diffusion.

As illustrated in FIG. 1, the reservoir 11 behind the tip 4 of the transducer 1 is mainly conical, having a larger conicity C than a conicity c of the reaction chamber. In the shown embodiment the conicity of the reaction chamber is zero. A relative increase in volume of the reservoir 11 along a longitudinal centre line A for the microsensor is, therefore, bigger than a corresponding relative increase in volume of the reaction chamber 10. Consequently, a "dilution" takes place, i.e. a dilution of the part of secondary medium which has not been consumed by the transducer and that has diffused through the passage 12. This means that an error-contribution originating from the surplus of the secondary medium in the reservoir 11 behind the tip 4 of the transducer 1 can be ignored.

Figure 2:
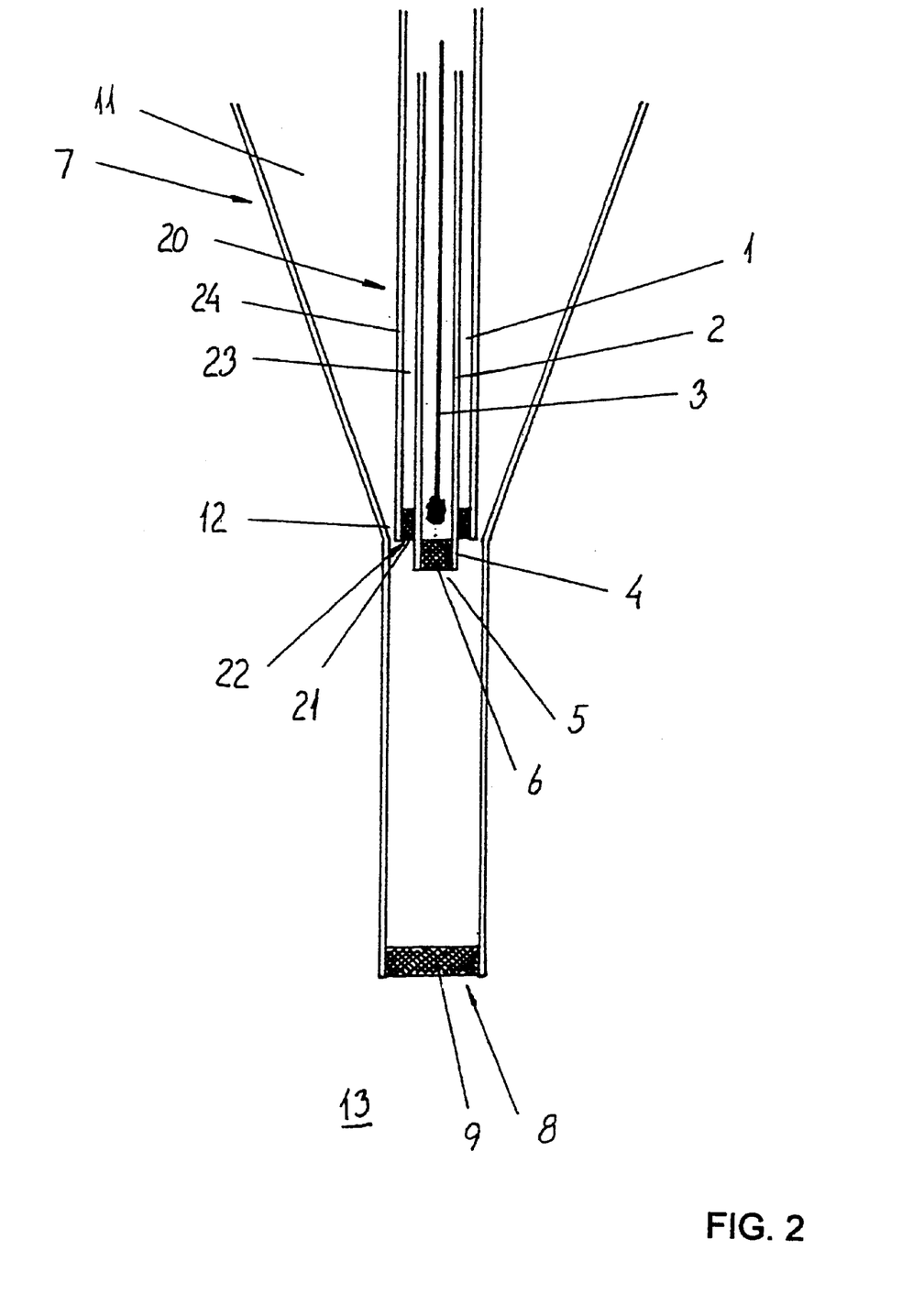
FIG. 2 A drawing showing a second embodiment of the microsensor according to the invention.

FIG. 2 shows a second embodiment of a microsensor according to the invention. The microsensor shown in FIG. 2 has a so-called window 20 which surrounds the transducer 1 and the casing 7. The window 20 stretches behind the tip 4 of the transducer 1 and has a diffusion-open plug 21, placed in an opening 22 of the window 20. The window 20 is intended for carrying away the secondary medium that diffuses through the passage 12, and which may contribute to measuring errors. The need for "dilution" of nitrous oxide by means of a conicity of the reservoir 11 is thereby eliminated. A reservoir 23 in the window 20 between the transducer 1 and a wall 24 for the window 20 contains a gas. The gas in the reservoir 23 can be atmospheric air, however, preferably an oxygen-free gas.

Figure 3:
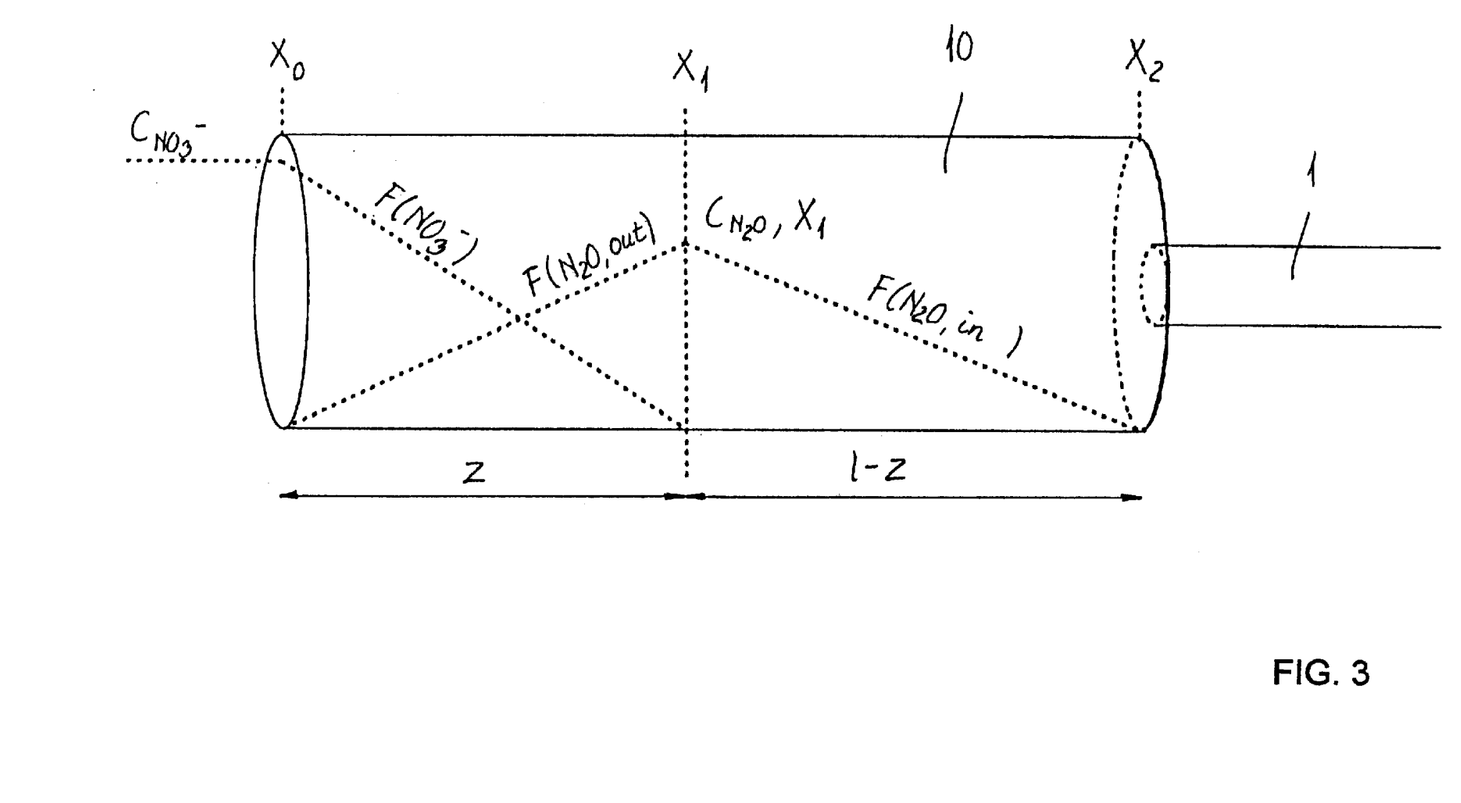
FIG. 3 A drawing of a flux of $NO_3^-$ and $N_2O$ in the reaction chamber of the microsensor.

Measurements by means of the microsensor basicaly take place as mentioned above in connection with bacterial reduction of $NO_3^-$ to $N_2O$ and a subsequent electrochemical detection of the produced $N_2O$. Immobilised bacteria are constantly supplied with electron donors and nutrients by diffusion from the reservoir 11 stretching behind the tip 5 of the transducer 1. The volume containing nutrient in the reservoir is so big relatively to the amount of bacteria in the reaction chamber, that the bacteria in practice is fed from a constant source ensuring a long life time. The substrate incorporates micro nutrients and either electron donors or acceptors depending on the primary medium in the reaction chamber. In this sensor, the primary medium is nitrate, $NO_3^-$, which is an electron acceptor. Hence the substrate contains an electron donor. For example, Tryptic Soy Broth (TSB) can advantageously be used as substrate, because it contains both micro nutrients and electron donor. The bacteria in the reaction chamber 10 are facultatively anaerobic and are able to oxidize organic material from the reaction chamber 10 at the presence of oxygen, $O_2$, or $NO_3^-$, being electron acceptors. The bacteria nearest to the opening of the reaction chamber 10 reduce all oxygen, $O_2$, that diffuses into the reaction chamber 10. Therefore, the main part of the reaction chamber 10 is anoxic, and denitrification resulting in production of $N_2O$ will be the only way of respiration for the greater part of the bacteria in the reaction chamber 10. A proportional part of the produced $N_2O$ from the reduction of $NO_3^-$ will diffuse into the transducer, where $N_2O$ will be reduced by the negatively charged cathode 3 (see FIG. 1). The reduction produces an electron flow from the anode to the cathode 3, which is measured with a pico-amperemeter, and the electron flow is directly proportional to a $N_2O$ flux into the transducer. A small fraction of $N_2O$ diffuses through the passage 12 in opposite direction to the nutrients, and the rest diffusies out to the external medium FIG. 3 is a drawing of a cylindric reaction chamber 10 of a microsensor according to the invention. In the following explanation, the reduction zone is depicted as a point-topoint connection and the reaction chamber is considered cylindrical. It will be shown that a microsensor according to the invention, where the reduction zone has a length and/or a conic reaction chamber, can provide a current signal that is linearly dependent on the concentration of $NO_3^-$. The $NO_3^-$ flux into the reaction chamber 10 is described by Ficks law of diffusion (Ficks First Law):S $$F(NO_3^-)=D(NO_3^-)\cdot(C(NO_3^-), X0/z$$

where F is the flux, D is the coefficient of diffusion, $C,X_0$ is the concentration in a position $X_0$ at the opening of the reaction chamber, and z is a distance from the opening of the reaction chamber to a position $X_1$ along a length L of the reaction chamber, the concentration $C(NO_3^-)$ being zero at $X_1$.

Making stoichiometric considerations Ficks First Law can be determined by means of the following formula $$F(NO_3^-)=2\cdot(F(N_2O,out)+F(N_2O,in))$$

where $F(N_2O,out)$ is the flux of $N_2O$ out of the reaction chamber, and $F(N_2O,in)$ is the parameter determining the signal of the transducer. The flux of $N_2O$ can be calculated by Ficks First Law:

$$F(N_2O,in)=D(N_2O)\cdot C(N_2O), X_1/(L-z) \text{ and}$$

$$F(N_2O,out)=D(N_2O)\cdot C(N_2O), X_1/z$$

This gives four equations with $F(NO_3^-), z, F(N_2O,out)$ $F(N_2O,in)$ and $C(N_2O,X_1)$ being the unknowns. A substitution of the equations in relation to each other gives the following equation for the flux:

$$F(N_2O,in)=(0,5\cdot C(NO_3^-)\cdot D(NO_3^-))/L$$

and this gives the following equation for the flow $$Flow(N_2O,in)=F(N_2O,in)\cdot A=\pi/2\cdot C(NO_3^-)\cdot D(NO_3^-)\cdot r^2/L,$$

where A is the area of the sectional view of the reaction chamber and r is the radius of the sectional view of the reaction chamber. This equation shows, that the $N_2O$ flux into the transducer is independent on the position of $X_1$ for an $NO_3^-$ reducing zone in the reaction chamber, and that the flux is linearly proportional to the $NO_3^-$ concentration. As the $N_2O$ gradient from the position $X_1$ to the transducer is independent on the position of $X_1$, and independent on whether the $NO_3^-$ that diffuses into the reaction chamber is reduced before or after the position $X_1$, changes in the $O_2$ concentration will not influence the $NO_3^-$ measurements.

If the microsensor is exposed to environments with higher concentrations of $NO_3^-$, the reaction zone will be extended and $NO_3^-$ will diffuse further into the reaction chamber. $NO_3^-$ concentrations outside the opening of the transducer where $NO_3^-$ concentrations that have not been reduced, diffuse right to the opening 5 of the transducer, form the highest kind of concentration for measuring a linear signal. Higher $NO_3^-$ concentrations outside the opening 8 of the reaction chamber results in a non-linear signal.

The capacity of the bacteria for the reduction of $NO_3^-$ depends on the length of the anoxic zone in front of the transducer and the activity of the bacteria. The maximum $NO_3^-$ concentration which can be determined by means of the microsensor, therefore, depends on whether the environment is oxic or anoxic. The presence of a physical or chemical substance in the environment, where measurement takes place, which influences negatively upon the bacterial activity will, therefore, limit the maximum $NO_3^-$ concentration which the microsensor is able to measure. However, the physical or chemical substance will not influence upon the signal as long as the bacteria are sufficiently active to prevent $NO_3^-$ from reaching the transducer tip.

Figure 4:
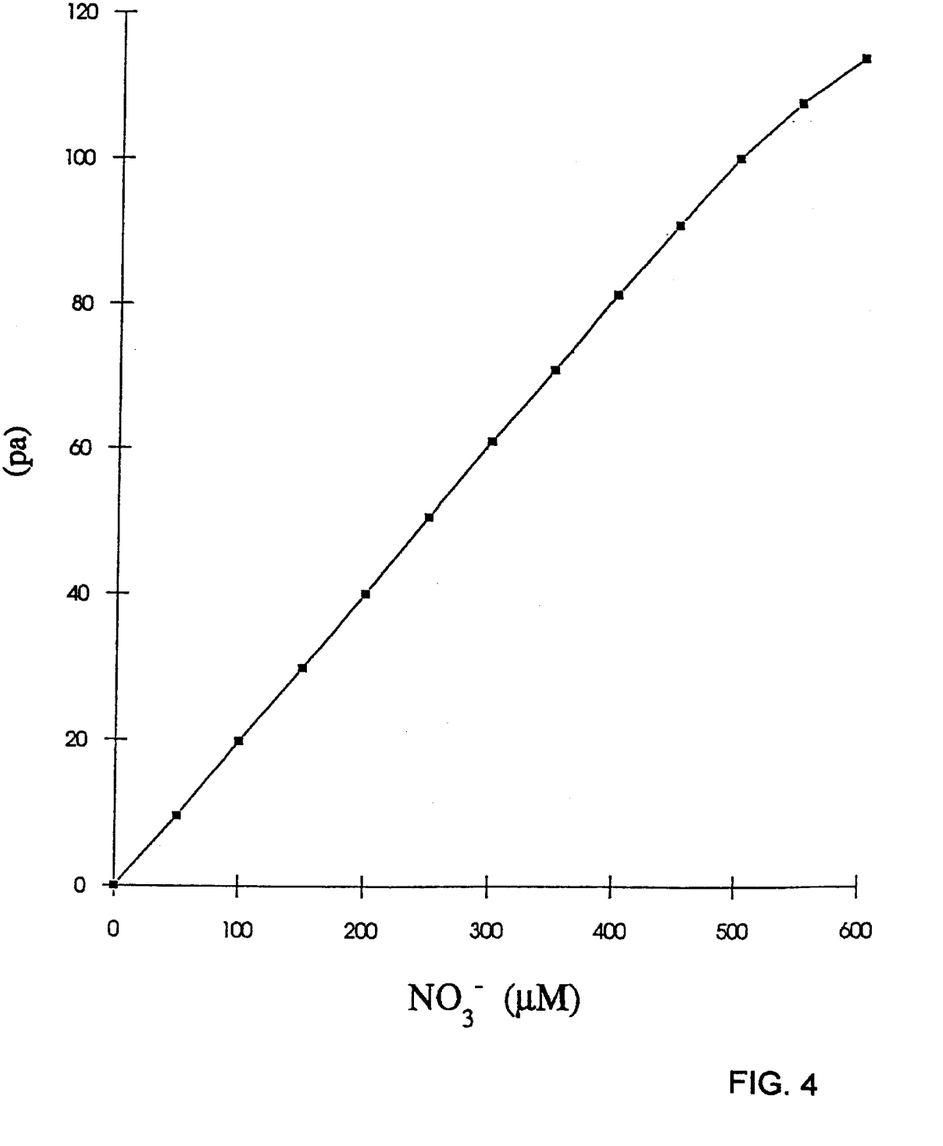
FIG. 4 A graphic showing a calibration curve for the microsensor.

FIG. 4 illustrates a calibration curve for a microsensor according to the invention. The microsensor calibrated is a nitrate microsensor type intended for measurement of the presence and the concentration of nitrate $NO_3^-$. The measurement has been done by determining a response from the transducer, measured in pico ampere (pA), as a function of the concentration of $NO_3^-$ in an environment outside the membrane in the opening of the casing. The curve shows that the response from the transducer is directly proportional to the $NO_3^-$ concentration in the environment up to a concentration of 500 $\mu$M $NO_3^-$. At concentrations exceeding 500 $\mu$M $NO_3^-$ a gradual reduction of the gradient for the graphic curve takes place.

Figure 5:
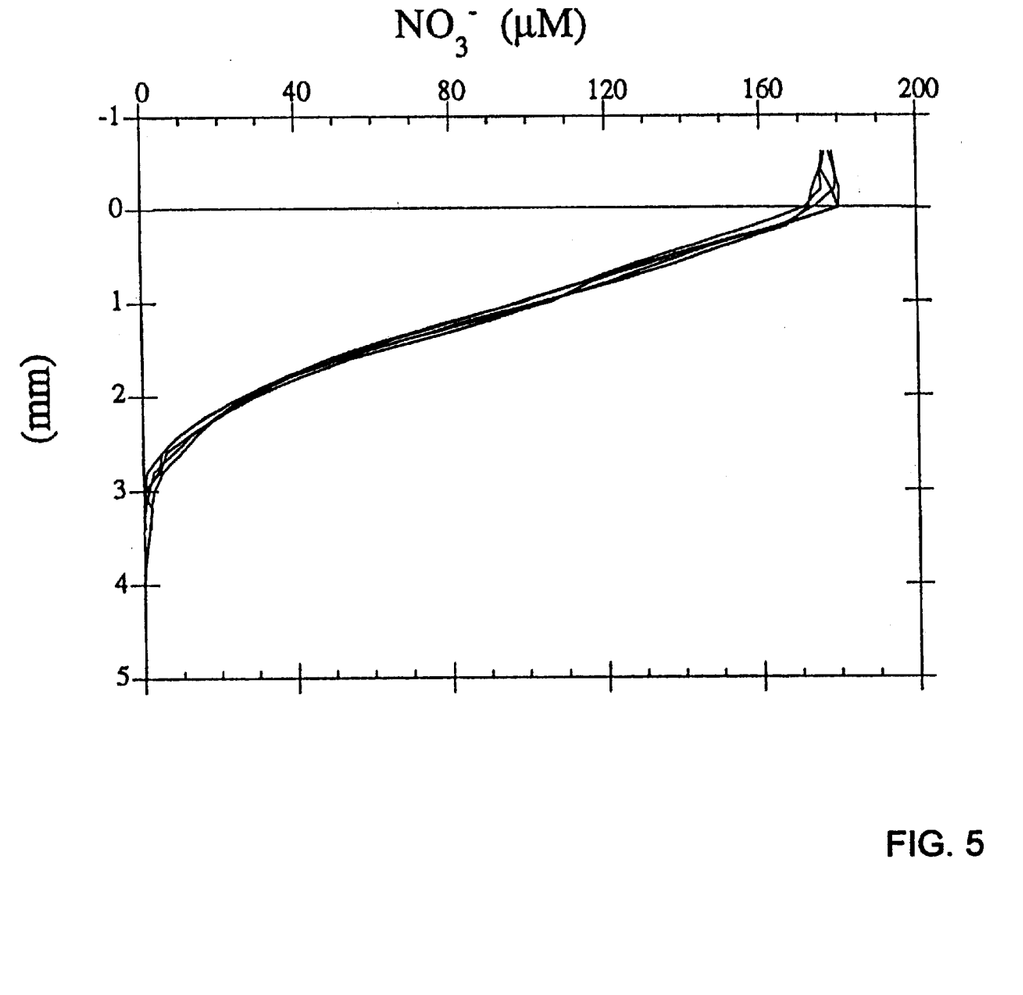
FIG. 5 A graphic showing a curve with measurements of the presence and the concentration of nitrate in a sediment.

FIG. 5 is a graphic curve illustrating several measurements done with the microsensor. The measurements have been performed in a sediment where the depth of a sediment on the sea bottom is determined as a function of the concentration of nitrate, $NO_3^-$, in the sediment. The graphic curve shows that the concentration of $NO_3^-$ in the surface of the sediment, which corresponds to a depth of 0 mm, is between 170 and 180 $\mu$M. The deeper the measurements are carried out in the sediment, the lower the $NO_3^-$ concentration. At a depth of about 3 mm in the sediment the $NO_3^-$ concentration is reduced to about 0 $\mu$M. The curve illustrates that the sediment takes up $NO_3^-$ from the water above the sediment and that $NO_3^-$ is being consumed due to denitrification.

The invention is described above with reference to specific embodiments for a microsensor. However, other kinds of embodiments are applicable. Sizes and ranges can have other values, and other kinds of material than those already stated, could be used. A membrane of another material than a non degradable polymer, for example hydrogels can be used, as well as other kinds of transducers than the one mentioned, for example fibre optical transducers. The inventive microsensor can also be used for the measurement of the presence and concentration of other substances than nitrate, $NO_3^-$, for example sulphate, $SO_4^{--}$, if the transducer is a $H_2S$ tranducer and the bacteria in the reaction chamber are $SO_4^{--}$ reducing.

What is claimed is:

1. Microsensor for measurement of the presence and the concentration of a primary substance in a liquid, a gas or a matrix, the microsensor comprising a casing surrounding a reaction chamber and a transducer located in the casing, the reaction chamber being located between a tip of the transducer and an opening of the casing and containing a biologically active substance which metabolises the primary substance to a secondary substance, the transducer measuring the concentration of the secondary substance, and in which the casing delimits a reservoir containing nutrients, where the nutrients rest against the casing, and including a passage located between the reaction chamber and the reservoir through which nutrients diffuse from the reservoir to the reaction chamber and through which the secondary substance diffuses away from the reaction chamber.

2. Microsensor according to claim 1 in which the casing surrounds both reaction chamber and reservoir.

3. Microsensor according to claim 1 in which the passage is defined between the transducer and the casing.

4. Microsensor according to claim 1 in which the nutrients located in the reservoir contain a substrate incorporating micro nutrients and an electron acceptor or an electron donor.

5. Microsensor according to claim 1, in which the passage includes means for facilitating or influencing the diffusion of a nutrient or a second substance.

6. Microsensor according to claim 5, in which the means comprises a conicity of the casing and the conicity of a part of the casing surrounding the reservoir is larger than the conicity of a part surrounding the reaction chamber.

7. Microsensor according to claim 6 in which only the part of the casing surrounding the reservoir is conical, and the part enclosing the reaction chamber has parallel sides.

8. Microsensor according to claim 5, in which the means consist of a window which is located between the transducer and the casing and surrounds the transducer, the window having an opening which is positioned behind a transducer detection zone, the opening containing a diffusion-open barrier.

9. Microsensor according to claim 8, in which the window contains a non-oxygen containing gas.

10. Microsensor according to claim 8 in which walls of the casing are essentially parallel to walls of the window.

11. Microsensor according to claim 1 in which the reaction chamber contains nitrate reducing bateria, the primary substance is nitrate ($NO_3^-$), the secondary substance is nitrous oxide ($N_2O$), the bacteria reduces nitrate ($NO_3^-$) and produces nitrous oxide ($N_2O$), and the transducer detects the nitrous oxide ($N_2O$).

12. Microsensor according to claim 1 in which the transducer is an electro-chemical detector.

13. Microsensor according to claim 1 in which the transducer is a fibre optical detector.

14. Microsensor according to claim 1 in which a membrane is located proximate an opening of the reaction chamber.

15. Microsensor for measurement of the presence and the concentration of a primary substance in an environment comprising a liquid, gas or matrix, the microsensor comprising a casing with a reaction chamber and an opening which is located between the environment and the reaction chamber for transport of the primary substance from the environment into the reaction chamber, a biologically active material being located in the reaction chamber for the transformation of the primary substance into a secondary substance, and including a transducer for measuring the secondary substance, the transducer having a detection zone located a distance from the opening, the reaction chamber extending between a transducer detection zone and the opening, the casing having a reservoir which essentially contains no secondary substance, and including a passage between the reaction chamber and the reservoir, the reservoir containing a substrate for the nutrition of the biologically active material.

16. Microsensor according to claim 15, in which the reaction chamber contains a liquid or a matrix with biological components, the reservoir includes a medium which essentially does not contain any secondary substance, and the passage between the reaction chamber and the reservoir has a diffusion-open barrier, the diffusion-open barrier being located in a window between the reaction chamber and the reservoir.

17. Microsensor according to claim 15, in which the reaction chamber contains nitrate reducing bacteria, the primary substance is nitrate ($NO_3^-$), the secondary substance is nitrous oxide ($N_2O$), the bacteria reduce nitrate ($NO_3^-$) in producing nitrous oxide ($N_2O$), and the transducer detects the nitrous oxide ($N_2O$).

18. Microsensor according to claim 15, in which the microsensor has a window, the window surrounding the transducer and being located between the transducer and the casing, the window having an opening which is located behind the transducer detection zone, and the opening including a diffusion-open barrier.

19. Microsensor according to claim 15, in which the reaction chamber contains a liquid or a matrix with the biological components, the reservoir contains a liquid or a matrix, the passage between the reaction chamber and the reservoir extends as a channel, and the channel has a cross section which increases in a direction away from the reaction chamber.

\* \* \* \* \*